United States Patent [19]

Raisfeld

[11] Patent Number: 4,507,321
[45] Date of Patent: Mar. 26, 1985

[54] EPITHELIAL CELL GROWTH REGULATING COMPOSITION CONTAINING POLYAMINES AND A METHOD OF USING SAME

[75] Inventor: Ilene H. Raisfeld, Setauket, N.Y.

[73] Assignee: The Research Foundation of State University of New York, Albany, N.Y.

[21] Appl. No.: 349,598

[22] Filed: Feb. 17, 1982

[51] Int. Cl.³ .................... A61K 31/13; A61K 31/155
[52] U.S. Cl. .................................. 514/673; 424/326; 514/674; 514/927
[58] Field of Search ............................... 424/325, 326

[56] References Cited

U.S. PATENT DOCUMENTS 4,182,891  1/1980  Metcalf et al. ..................... 424/320
4,207,315  6/1980  Voorhees et al. ................... 424/325

OTHER PUBLICATIONS

*Index of Tumor Chemotherapy*, Dyer, pp. 10–12, 65, 72 and 73, (Mar. 1949).
CA 73: 11798e, Nishiyama, (1961).
CA 94: 206426t, Coffino, (1981).

*Primary Examiner*—Jerome D. Goldberg
*Assistant Examiner*—Freda L. Abramson
*Attorney, Agent, or Firm*—Omri M. Behr

[57] ABSTRACT

Disclosed herein are compositions containing aliphatic di- and polyamine, or agmatine which are useful to regulate, i.e., stimulate or inhibit, epithelial cell growth. The compositions containing low concentrations of these compounds, by virtue of their epithelial cell growth stimulating activity, are useful in promoting wound healing, treating burns, treating ischemic, debubitus and peptic ulcers, plastic and reconstructive surgery, dermatological disorders, promoting autograft and homograft growth, stimulating organ and tissue regeneration in vitro and in vivo, as a component in defined (serum protein-free) media for cultured cells.

Compositions containing these compounds in higher concentrations are useful in the inhibition of cell growth and are useful in the treatment of psoriasis and in retardation of fibrosis after injuries to the spinal cord and nervous system. Also disclosed are various methodologies for utilizing such compositions.

14 Claims, No Drawings

EPITHELIAL CELL GROWTH REGULATING COMPOSITION CONTAINING POLYAMINES AND A METHOD OF USING SAME

BACKGROUND OF THE INVENTION

The human body contains several types of tissues. One of the most important of these tissues is epithelial tissue, or epithelium. This epithelial tissue lines body cavities or organs and covers body surfaces. It forms the lining of all hollow organs, such as the intestines, bladder, trachea, and uterus. The external covering of the body, the epidermis of the skin, is also epithelium, as are the functional cells of glands. When the epithelial tissues of the human body are injured or contract a particular disease, it is often important that the epithelial cells regrow as quickly as possible in order to prevent serious illness or even death of the patient. An agent which stimulates epithelial cell growth could be utilized to promote wound healing, treat burns, treat ischemic, debubitus and peptic ulcers, in plastic and reconstructive surgery, in dermatologic disorders, in promoting autograft and homograft growth, in stimulating organ and tissue regeneration in vitro and in vivo, and as an essential component in defined (serum-protein free) media for cultured cells, organs, and tissues.

In other instances, it is advisable to inhibit or retard epithelial cell growth.

In contrast to epithelial cells, fibroblasts are cells which proliferate and elaborate collagen, thereby forming scar tissue. Excessive scar tissue formation is often undesirable.

An agent which inhibits fibroblast growth could be particularly useful in plastic and reconstructive surgery, such as in the control of scar formation and promotion of nerve regeneration following injuries to the spinal cord and nervous system. Such an agent applied in a concentration which retards epithelial cell growth could be utilized for the treatment of dermatological disorders characterized by a rapid proliferation of epithelial cell growth, such as psoriasis.

SUMMARY OF THE INVENTION

The present invention relates to composition containing polyamines which act as epithelial cell growth regulators, i.e. stimulants and inhibitors. Many of these compounds have been found in the body but their precise functions have not been recognized nor has their pharmacologic use. The finding that synthetic compounds can be used in the treatment of disorders of epithelial cell and fibroblast growth forms the basis of this application.

With respect to the growth of epithelial cells, the nature of the dose response provides that low concentrations of the polyamines of the present invention stimulate epithelial and fibroblast growth, while higher concentrations are inhibitory. Moreover, depending on the structure of a particular compound, the growth of epithelial cells can be stimulated over and above that of fibroblasts. More particularly, this invention relates to compositions containing a cell growth regulating, i.e. stimulating or inhibiting, amount of a compound selected from the group consisting of aliphatic di- and polyamines with straight or branched chains of length from 2 to 14 carbon atoms long bearing 2 to 6 amine groups, and agmatine; and the pharmaceutically acceptable acid addition salts thereof. Many of these compounds have been found in the body but their precise functions have not been recognized nor has their pharmacologic use. The finding that synthetic compounds can be used in the treatment of disorders of epithelial cell and fibroblast growth forms the basis of this application.

The epithelial cell growth regulating agents of this invention may be utilized as their free bases or as their pharmaceutically acceptable acid addition salts. Such acid addition salts can be derived from a variety of inorganic and organic acids such as: hydrochloric, sulfuric, phosphoric, methanesulfonic, sulfamic, citric, lactic, pyruvic, oxalic, maleic, stearic, succinic, tartaric, fumaric, cinnamic, aspartic, acetic, benzoic, salicylic, gluconic, ascorbic and related acids. The acid salts lack the odor of the free bases, which is an additional advantage in treatment.

The aliphatic di- and polyamines referred to above contain 2 to 14 carbon atoms and are derived from alkanes, such as n-propane, isopropane, butane, isobutane, tert-butane, hexane, isohexane, heptane, octane, nonane, decane, and dodecane. The corresponding branch chain analogs of these groups are also included.

The 2 to 6 amine group contained by the aliphatic di-and polyamines may be either primary or secondary and may be located either in a terminal position, within the alkane chain, or both.

Preferred compounds for use in the compositions and methods of the present invention are: spermidine(4,4'-iminobis butylamine), spermine, and putrescine(1,4-diaminobutane).

DETAILED DESCRIPTION OF THE INVENTION

The compounds useful in the composition and methods of the present invention are known in the chemical art. Details of the synthetic preparation of many of the compounds utilizable in the compositions and methods of the present invention may be found in *Beilsteins Handbuch Der Organischen Chemie*. *The Merck Index*, 9th edition, also references many of the preferred compounds of this invention.

The preferred compounds useful in the compositions and methods of the present invention are encompassed by the following formula 1:

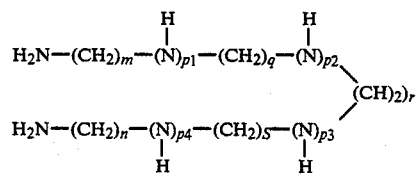

wherein $p_1$, $p_2$, $p_3$, $p_4$ are independently 0 or 1; m, n are independently 1-7; q, r, s are independently 0-7; with the provisos that $n+m+q+r+s$ are less than or equal to 14. Highly preferred compounds of formula 1 are those wherein m is 3, n is 4, $p_2$, $p_3$, $p_4$, q, r, and s are 0 and $p_1$ is 1; m is 4, $p_1$, $p_2$, $p_3$, $p_4$, q, r, s, and n are 0; and m is 3, q is 4, r is 3, $p_1$ and $p_2$ are 1, $p_3$ and $p_4$ are 0, and s is 0.

Specific compounds utilizable in the composition and methods of the present invention are the following: (a reference indicated in [ ] immediately following each compound is a reference to the chemical preparation of the compound):

Spermidine(4,4'-iminobisbutylamine) [*Beil.* 4 (2) 704];

Spermine, [Beil. 4 (2) 704], Merck Index 9,8515];
Putrescine(1,4-diaminobutane) [Beil. 4 264];
1,3-diaminopropane, [Beil. 4 261];
Agmatine, [(4-aminobutyl)guanidine], [Beil. 4(1)420,– Merck Index 9, 176];
1,2-diaminopropane, [Beil 4, 257, Merck Index 9, 7641];
1,10-diaminodecane, [Beil 4, 273];
1,12-diaminododecane, [Beil. 4 273];
3,3'-iminobispropylamine, [Biochem Biophys. Res. Commun., 63, 69(1975)];
1,7-diaminoheptane, [Beil. 4, 271];
1,6-diaminohexane, [Beil. 4, 269, Merck Index 9,4564];
1,2-diamino-2-methylpropane, [Beil. 4, 266]
1,9-diaminononane, [Beil. 4, 272];
1,8-diaminooctane, [Beil. 4, 271]; Cadaverine, [1,5-diaminopentane, [Beil. 4, 266, Merck Index 9, 6914];
triethylenetetraamine, [Beil. 4, 255, Fieser, Reagents for Organic Synthesis, 1, 1204];
triethylenetetraamine tetrahydrochloride, [Beil. 4, 255];
N-(2-aminoethyl)-1,3-propanediamine;
diethylenetriamine, [Beil. 4, 255];
ethylenediamine, [Beil. 4, 230, Merck Index, 9,3731, Fieser, Reagents for Organic Synthesis, 1, 372, 4, 231];
ethylenediamine dihydrochloride [Beil. 4, 230, Merck Index, 9, 3731]; and
tetraethylenepentamine.

The free base form of the compounds utilizable in the present invention may be conveniently converted to the corresponding acid addition salt by contacting a solution of the free base with the appropriate acid. Particularly preferred salts are the acid addition salts formed with hydrochloric and sulfuric acids, e.g., hydrochloride and sulfate.

The epithelial cell regulating activity of the compounds utilizable in the composition method of the present invention may be determined by measurement of the effect of the test compound in a screening assay for ability of a test compound to promote or inhibit wound closure in skin. The term "wound healing" is used to denote decreased wound surface area without implying a mechanism of action. One model utilized is the unoccluded excision model in guinea pigs and mice.

The compositions of the present invention comprise one or more of the above-mentioned compounds in an epithelial cell regulating amount together with a suitable pharmaceutical carrier. An epithelial cell regulating amount is defined as the amount of compound necessary to cause epithelial cell growth at a rate higher than an untreated state (stimulating amount), or as the amount necessary to cause epithelial cell growth to a rate slower than the untreated state (inhibitory amount). In the usual course of therapy, the active compound is incorporated into an acceptable vehicle to form a composition for topical administration to the affected area or into a form suitable for oral or parenteral administration, such as tablets, capsules, pills, suspensions, injectables, and solutions.

Compositions for topical application may be exemplified by ointments, creams, lotions, solutions, suspensions, aerosols, gels, dusting powder, and impregnated bandages and dressings. Such compositions would normally be based upon standard carriers such as pharmaceutically acceptable vegetable oils and gelatins, gums and petrolatum. Other ingredients to the composition of the present invention may be preservatives, coloring, flavoring, sweetening, thickening, suspending, disbursing, emulsifiing, swelling, stabilizing and buffering agent as required by the specific formulation. Such compositions are envisioned to contain the active ingredient in from about 0.005% to about 5% by weight. For topical application, a concentration from about 0.05 micro moles to about 0.5 micro moles per gram vehicle is optimal for the stimulation of epithelial cell growth, while concentrations from about 0.5 micro moles to about 1 milli mole per gram vehicle inhibit cell growth (as in the treatment of keloids). The former concentrations of active components will here and after be referred to as "low concentrations" and the latter concentrations as "higher concentrations". It should be pointed out, however, that the dividing line between a dosage which stimulates growth and a dosage which inhibits growth is not precise and must be derived for a particular compound and a particular indication.

Compositions for oral or parenteral administration, other than the dosage units mentioned above are exemplified by lozenges, dragees, powders, granulates, solutions, suspensions or elixirs.

The required daily dosage for oral or parenteral administration may be administered in single or divided dosages. The optimal dosage for stimulation of cell growth is 0.2 to 10 millimoles per patient per 24 hours (or 0.003 to 0.14 m moles/kg body weight day). Higher dosages can be utilized where inhibition of cell growth is desired. In patients, the exact dosage to be administered will, of course, be dependent upon the particular compound employed, the disease or injury being treated, other diseases present, the age and weight of the subject, the hepatic and renal status and the subject patient's individual response. When the compositions of the present invention are utilized to promote wound healing, treat burns, treat dermatological disorders or in plastic or reconstructive surgery the amount of compound to be administered will depend on the acre of epithelial cells being treated.

Where the composition of the present invention is used to treat ischemic, decubitus, or peptic ulcers a combination of topical and systemic therapy may be employed, administered as single or divided daily dosages. When the compositions of the present invention are used to stimulate organ or tissue regeneration in vitro or in vivo the dosage administered will be tailored to the response of the particular organ or tissue involved. When the compositions of the present invention are added to a defined (serum protein-free) medium for culturing cells, organs, or tissues the amount utilized will be dependent additionally upon the type of cells, organs, or tissues.

When these compounds are used to inhibit cell growth, a combination of local perfusion, systemic and/or topical therapy may be employed.

The following examples describe in detail compositions illustrative of the present invention and methods for their utilization. It will be apparent to those skilled in the art that many modifications, both of materials and methods may be practiced without departing from the purpose and intent of the disclosure.

EXAMPLES

Example 1

Ointment formulation

| Ingredient | Amount |
| --- | --- |
| Spermidine, micronized | 0.05 micro moles-1 millimole |
| Mineral oil, USP | 50.0 mg |

-continued

| Ingredient | Amount |
| --- | --- |
| White Petrolatum, USP to make | 1.0 g |

Procedure:

A weighed quantity of white petrolatum and mineral oil is heated to 65° C. and uniformly mixed. The mixture is cooled to 50°-55° C. with stirring. The stated active ingredient which has been dispersed in a portion of the mineral oil and milled is added to the above with stirring. The ointment is cooled to room temperature.

This ointment containing low concentrations of the active component is utilizable to treat wounds, burns, dermatological disorders such as eczema, seborrheic dermatitis, anogenital and senile pruritis. The higher concentrations of the active components will be useful in suppressing cell growth as in the treatment of psoriasis.

Example 2

Jelly formulation

| Ingredient | Amount |
| --- | --- |
| Spermine, micronized | 0.05 micro moles-1 millimole |
| Water | 5 ml |
| K-Y ® Jelly* | 1.0 g |

*a water soluble jelly lubricant manufactured and trademarked by Johnson & Johnson, New Brunswick, NJ containing water, glycerine, sodium alginate, sodium carboxymethyl cellulose, propylene glycerol, potassium hydroxide, propylene oxide and chlorhexidine glyconate preservative.

Procedure:

A weighed quantity of white petrolatum and mineral oil is heated to 65° C. and uniformly mixed. The mixture is cooled to 50°-55° C. with stirring. The stated active ingredient which has been dispersed in a portion of the mineral oil and milled is added to the above with stirring. The ointment is cooled to room temperature.

This ointment containing low concentration of the active agent is utilizable to treat wounds, burns, dermatological disorders such as eczema, seborrheic dermatitis, anogenital and senile pruritis. Compositions containing the higher concentrations are useful in suppressing cell growth, as in the treatment of psoriasis.

Example 3

Ointment formulation

| Ingredient | Amount |
| --- | --- |
| Putrescine | 0.05 micro moles-1 millimole |
| Mineral oil, USP | 50.0 mg |
| White Petrolatum, USP to make | 1.0 g |

A weighed quantity of white petrolatum and a mineral oil is heated to 65° C. and uniformly mixed. The mixture is cooled to 50°-55° C. with stirring. The stated active ingredient which has been dispersed in a portion of the mineral oil and milled is added to the above with stirring. The ointment is cooled to room temperature.

This ointment containing the lower concentrations of the active compound is utilizable to treat wounds, burns, dermatological disorders such as eczema, seborrheic dermatitis, anogenital and senile pruritis. Compositions containing the higher concentrations are useful in suppressing cell growth, as in the treatment of psoriasis.

In accordance with the above procedure, but where in place of the free base there are utilized in the acid addition salts with hydrochloric, sulfuric, phosphoric, methanesulfonic, sulfamic, citric, lactic, pyruvic, oxalic, maleic, stearic, succinic, tartaric, fumaric, cinnamic, aspartic, acetic, benzoic, salicylic, gluconic, ascorbic acids and a similar product is obtained.

Example 4

Ointment formulation

| Ingredient | Amount |
| --- | --- |
| Spermidine, micronized | 0.05 micro moles-1 millimole |
| Mineral oil, USP | 50.0 mg |
| White Petrolatum, USP to make | 1.0 G |

Procedure:

A weighed quantity of white petrolatum and mineral oil is heated to 65° C. and uniformly mixed. The mixture is cooled to 50°-55° C. with stirring. The stated active ingredient which has been dispersed in a portion of the mineral oil and milled is added to the above with stirring. The ointment is cooled to room temperature. This ointment containing the lower concentrations of the active compound is utilizable to treat wounds, burns, dermatological disorders such as eczema, seborrheic dermatitis, anogenital and senile pruritis. Compositions containing the higher concentrations are useful in suppressing cell growth, as in the treatment of psoriasis.

In accordance with the above procedure, but where in place of spermidine, there is utilized spermine, or agmatine sulfate, a similar composition is obtained.

Example 5

Lotion formulation

| Ingredient | Amount |
| --- | --- |
| Spermidine, micronized | 0.05 micro moles-1 millimole |
| Aluminum monostearate | 50.0 mg |
| isopropyl myristate to make | 1.0 g |

About 90% of the required isopropyl myristate is heated to 60° C. and aluminum and monostearate added with stirring and maintenance of heat to dissolve the aluminum monostearate. The active ingredient is dissolved in remaining quantity of isopropyl myristate. The solution of the active ingredient is added to the thickened solution of the aluminum minostearate in isopropyl myristate previously cooled to 45° C. with stirring. The lotion is cooled to room temperature with agitation.

This lotion containing the lower concentrations of the active compound may be utilized to treat a variety of wounds, burns, determatological disorders and to promote autograft or homograft growth. Compositions containing the higher concentrations are useful in suppressing cell growth, as in the treatment of psoriasis.

In accordance with the above procedure, but where in place of spermidine there is utilized spermine, agamtine, putrescine or cadaverine as free base or as any of the acid salts of acids set forth in Example 3 a similar lotion is obtained.

Example 6

Gel formulation

| Ingredient | Amount |
| --- | --- |
| Spermidine, micronized | 0.05 micro moles-1 millimole |
| Polyethylenes and Copolymers (A-C8) | 100.0 mg |
| Mineral oil, light to make | 1.0 g |

Procedure:

A portion of the mineral oil (about 90%) in a suitable vessel is heated to about 80° C., and polyethylene (A-C8) added to the mineral oil. The mixture is agitated slowly while hot until all the polyethylene is dissolved. The above mixture is cooled quickly by placing the vessel in a cooling bath of 10° to 15° C. and the agitation resumed at normal speed. Once the content of the vessel has reached approximately 45° C., a solution of the active ingredient which was dissolved in the remaining mineral oil at 45° C. is added to the above polymer solution. The mixture is air cooled with slow agitation. This will result in a gel form.

This gel containing the active component at lower concentration is utilizable in the treatment of wounds, burns, dermatological disorders such as enumerated in Example 1, and in promoting autograft and/or homograft growth. Compositions containing the higher concentrations are useful in suppressing cell growth, as in the treatment of psoriasis.

In accordance with the above procedure, but where in place of spermidine there is utilized spermine, agmatine or putrescine either as free base or as any of the salts of acids set forth in Example 3, a similar lotion is obtained.

Example 7

Intramuscular or Subcutaneous oil injectable

| Ingredient | Amount |
| --- | --- |
| Spermidine | 0.05 micro moles-1 millimole/ml |
| Aluminum monostearate, USP | 20.0 mg/ml |
| Sesame oil, heat treated, USP q.s. ad. | 1.0 ml |

The above ingredients are mixed together and filled into sterile ampules. This injectable formulation containing the lower concentrations can be used to treat dermatological disorders such as enumerated in Example 1, to promote autograft and homograft growth, and to treat ischemic, decubitus and peptic ulcers. Compositions containing the higher concentrations are useful in suppressing cell growth, as in the treatment of psoriasis. Such a formulation may be administered by intralesional as well as by intramuscular and subcutaneous routes.

In accordance with the above procedure, but where in place of spermidine there is utilized spermine, agmatine, or putrescine either as free base or as any of the salts of acids set forth in Example 3, a similar injectable is obtained.

Example 8

Aerosol formulation

| Ingredient | Amount |
| --- | --- |
| Spermidine, micronized | 10.0 to 50.0 mg |
| Oleic Acid | 1.0 mg |
| Fluorotrichloromethane | 4,739.0 mg |
| Dichlorodifluoromethane | 12,250.0 mg |

Procedure:

Oleic acid is added to previously cooled fluorotrichloromethane and mixed with a high shear mixer. During mixing, the required amount of the active ingredient is added and mixing continued until homogeneous. If necessary, the suspension is adjusted to the required weight with fluorotrichlormethane. The required amount of suspension is metered into each aerosol canister, the valves are crimped onto the canister which is pressure filled through valves with the required amount of dichlorodifluoromethane. This aerosol formulation can be utilized in the treatment of wounds, burns, ulcerations, and dermatological disorders where extremely sensitive areas prevent manual application of such compositions as creams, ointments, lotions etc.

In accordance with the above procedure, but where in place of spermidine there is utilized spermine, agmatine or putrescine either as free base or as any of the acid salts of acids set forth in Example 3, a similar aerosol is obtained.

Example 9

Tablet formulation

| Ingredient | Amount |
| --- | --- |
| Spermidine | 0.05-10 millimoles per tablet |
| Lactose, direct compression grade | 173 mg |
| Microcrystalline cellulose | 30 mg |
| Sodium lauryl sulfate | 20 mg |
| Corn Starch | 25 mg |
| Magnesium stearate | 2 mg |

The stated active ingredients, lactose, microcrystalline cellulose, sodium lauryl sulfate and corn starch are mixed together and passed through a No. 46 screen. Magnesium stearate, is added and the product mixed and compressed into the desired shape on the tablet machine.

This tablet formulation may be utilized to treat various injuries and disease states in which an oral route of administration is desirable, e.g. peptic ulcers, burns and trauma, and inflammatory bowel diseases such as ulcerative colitis.

In accordance with the above procedure but utilizing spermine, putrescine, and agmatine sulfate in place of the spermidine, a similar product is obtained.

Example 10

Capsule formulation

| Ingredient | Amount |
| --- | --- |
| Spermidine, micronized | 50 mg |
| Lactose, USP | 173 mg |
| Microcrystalline cellulose | 30 mg |
| Sodium lauryl sulfate | 20 mg |
| Corn starch | 25 mg |
| Magnesium stearate | 2 mg |

Procedure:

Mix together the active ingredient, lactose, micrystalline cellulose, sodium lauryl sulfate and corn starch. Pass through a No. 80 screen. Add magnesium stearate, mix and encapsulate into the proper size 2-piece gelatin capsule. This capsule may be used wherever an oral dosage route is desired such as the injury and disease state enumerated in Example 9.

In accordance with the above product but utilizing spermine, putrescine, or agmatine sulfate in place of the spermidine, a similar product is obtained.

Example 11

Powder formulation

| Ingredient | Amount |
|---|---|
| Spermidine, micronized | 0.2–10 millimoles |
| Lactose | 150 g |

Mix the above powder with 8 ounces water and administer orally (with added flavorings) or with 32 ounces water to be utilized as a drench to impregnate or soak bandages.

This type of formulation can be administered orally wherever an oral dosage route is desired or topically wherever such a regimen is necessary.

By utilizing spermine, putrescine or agmatine sulfate in place of spermidine, a similarly useful composition is obtained.

Test Example

Male, C.D.-1 retired breeder mice, 30 gram body weight and male Hartley guinea pigs (450 Grams) were fed and housed under standard conditions. 24 hours before wounding, animals were anesthetized with sodium pentobarbital (mice) or chloral hydrate (guinea pigs), and the skin was prepared by shaving with an electric razor and Nair. Test compounds in 0.9% sodium chloride were dissolved in a constant weight of previous liquidfied K-Y-Jelly. An equal volume of sodium chloride was added to the vehicle as control.

On the day of wounding, animals were anesthetized and handled in groups of 6 according to a precise time schedule. Trephines were used to incise wounds 3 centimeters in diameter in the guinea pig and 1.5 centimeters in diameter in the mouse; skin was excised with flash sterilized iris scissors. Animals were randomly assigned to 6 categories—no vehicle, vehicle, and test compound 0.03 micro moles, test compound 0.197 micro moles, test compound 0.393 micro moles, test compound 0.785 micro moles, test compound 3.14 micro moles per 1 gram vehicle per wound. Each experiment was performed at least twice, with 10 animals in each treatment group.

Immediately after wounding and five minutes before application of the test compound the wound was photographed with a fixed lens focus and magnification. The time of the photograph is recorded as 0 time. Wounds were photographed again 4.5 hours later. Four days after wounding the eschar was peeled and wounds were photographed 96.5 hours after the first photograph.

Wound surface area was measured by projecting 35 millimeter slides of the wounds and tracing outlines on papers which were then cut out and weighed. Corresponding measurements were made by planimetry directly on the slide. The change in weight of paper or area by planimetry was designated as percent "healing". Both methods yielded the same information.

In this assay, at four hours, a representative compound of this invention, i.e. spermidine at a concentration of 0.197 micro moles effected a 42% decrease in wound area in comparison to 24% for the vehicle alone (p less than 0.005); a concentration of 0.393 micro moles spermidine effected a 23% decrease (p less than 0.005). At 96.5 hours, 0.197 micro moles spermidine produced a 65% reduction in wound size compared to a 49% decrease produced by the vehicle alone (p less than 0.005).

In contrast to the reduced wound area by the latter concentrations, spermidine, 3,14 micromoles effected a 100% increase in wound size in comparison to vehicle along (p less than 0.005).

Test Example

Monolayer cultures of mouse lung fibroblasts were grown to confluence in petri dishes under standard conditions, in medium containing serum. The medium was then changed to fresh, serum free medium, and cells were incubated for 36–48 hours longer. At this time cells were "wounded" by scraping an area equivalent to 20% of the cells off the plate, $^3$H-thymidine was added to all plates. To parallel cultures, putresine ($1 \times 10^{-9}$ M/L) or spermidine ($1 \times 10^{-9}$ M/L) were added. The course of wound healing was followed by visual observation using an ocular grid to count the number of cells moving into repair the original wound margins, and by 3H-thymidine uptake by autoradiography. Treated plates were compared to untreated wounded "controls". In comparison to untreated plates, 48 hours after wounding putrescine, $1 \times 10^{-9}$ M/L, significantly inhibited repair, and the cell-free zones were 50% larger. In contrast, the equivalent concentration of spermidine stimulated repair and, in comparison to untreated controls, the original wound margins contained 40% more cells.

What is claimed is:

1. A method of stimulating epithelial cell regrowth in wound healing which comprises administering to a human or animal in need to same an effective amount of an epithelial cell regrowth stimulating agent selected from the group consisting of: aliphatic di- and polyamines with straight- or branched-chain length from 7 to 14 carbon atoms long bearing 2 to 6 amine groups, and agmatine, and the pharmaceutically acceptable acid addition salts thereof.

2. A method in accordance with claim 1 wherein the route of administration is topical and comprises administering an effective amount of the regulating agent in a topically acceptable vehicle.

3. A method of claim 2 wherein the vehicle contains between 0.005 and 5% by weight of the stimulating agent.

4. A cell proliferation stimulating method of claim 2 which comprises administering between about 0.05 to about 0.5 micro moles of stimulating agent per gram of vehicle.

5. The method according to claim 1 wherein the route of administration is oral.

6. The method according to claim 1 wherein the route of administration is parenteral.

7. A method in accordance with claims 5 or 6 wherein the stimulating amount administered is between 0.003 and 0.14 milli moles per kilogram body weight per day.

8. A method according to claim 1 wherein the compound administered is spermidine or a pharmaceutically acceptable acid addition thereof.

9. The method according to claim 1 wherein the compound administered is spermine, or a pharmaceutically acceptable acid addition salt thereof.

10. A method according to claim 1 wherein the compound administered is agmatine, or a pharmaceutically acceptable acid addition salt thereof.

11. A method according to claim 1 wherein the wound is a burn.

12. A method according to claim 1 wherein the wound is a peptic ulcer.

13. A method of claim 1 which comprises administering an effective amount of an epithelial cell regrowth stimulating agent selected from the group of compounds of the formula

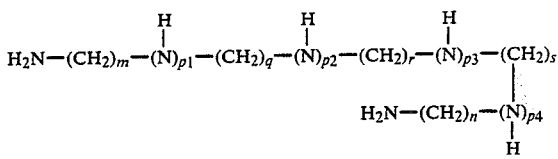

wherein $p_1$, $p_2$, $p_3$ and $p_4$ are independently 0 to 1; m, n are independently 1–7; q,r and s are independently 0–7; with the provisos that $n+m+q+r+s$ are greater than or equal to 7 and less than or equal to 14; and the pharmaceutically acceptable acid addition salts thereof.

14. A method of claim 13 wherein the epithelial cell stimulating compound is one wherein m is 3, n is 4, $p_2$, $p_3$, $p_4$, q, r and s are 0 and $p_1$ is 1; and m is 3, q is 4, r is 3, $p_1$ and $p_2$ are 1, $p_3$ and $p_4$ are 0, and s is 0.

* * * * *